United States Patent [19]

Haug et al.

[11] Patent Number: 5,079,384
[45] Date of Patent: Jan. 7, 1992

[54] HERBICIDAL (6-(HETERO)ARYLOXY-NAPHTHALEN-2-YL-OXY-ALKANECARBOXYLIC ACID DERIVATIVES

[75] Inventors: Michael Haug, Bergisch-Gladbach; Roland Andree, Langenfeld; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 263,498

[22] Filed: Oct. 27, 1988

[30] Foreign Application Priority Data

Nov. 3, 1987 [DE] Fed. Rep. of Germany ....... 3737179

[51] Int. Cl.⁵ ..................... C07C 69/76; A01N 37/36
[52] U.S. Cl. ..................... 560/56; 562/466; 562/840; 71/108
[58] Field of Search .................. 560/56; 562/466, 840; 71/108

[56] References Cited

U.S. PATENT DOCUMENTS 3,954,442  5/1976  Becker et al. ...................... 71/108

FOREIGN PATENT DOCUMENTS 3434447  3/1986  Fed. Rep. of Germany ........ 560/56
2010041  1/1987  Japan .

OTHER PUBLICATIONS

Chemical Abstracts, vol. 107, (1987).

Primary Examiner—Paul J. Killos
Attorney, Agent, or Firm—Sprung, Horn, Kramer & Woods

[57] ABSTRACT

Herbicidal (6-(hetero(aryloxy-naphthalen-2-yl-oxy)-alkanecarboxylic acid derivatives of the formula

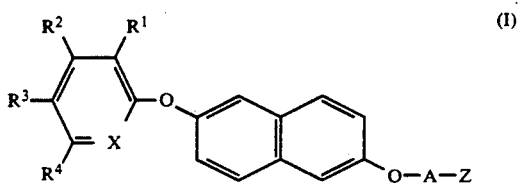

in which
$R^1$ stands for hydrogen, halogen, cyano or trifluoromethyl,
$R^2$ stands for hydrogen or halogen,
$R^3$ stands for halogen, trifluoromethyl, trifluomethoxy, trifluoromethylthio or trifluoromethylsulphonyl,
$R^4$ stands for hydrogen or halogen,
X stands for nitrogen or the grouping C—$R^5$,
in which
$R^5$ stands for hydrogen or halogen,
A stands for optionally branched alkanediyl and
Z stands for cyano or the grouping —CO—Y.

8 Claims, No Drawings

HERBICIDAL (6-(HETERO)ARYLOXY-NAPHTHALEN-2-YL-OXY-ALKANECARBOXYLIC ACID DERIVATIVES

The invention relates to new (6-(hetero)aryloxynaphthalen-2-yl-oxy)-alkanecarboxylic acid derivatives, processes and new intermediates for their preparation, and their use as herbicides.

It has already been disclosed that certain dioxy-benzene derivatives, such as, for example, methyl α-(4-(2,4-dichloro-phenoxy)-phenoxy)-propionate (diclofop-methyl) have herbicidal activity (cf. DE-OS (German Published Specification) 2,223,894). However, the action of these known compounds against weeds and their tolerance by crop plants are not always satisfactory.

New (6-(hetero)aryloxy-naphthalen-2-yl-oxy)-alkanecarboxylic acid derivatives of the general formula (I)

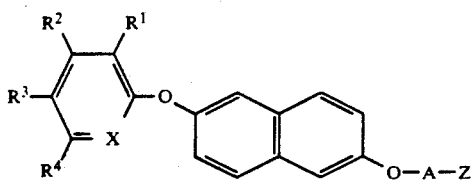

in which
$R^1$ stands for hydrogen, halogen, cyano or trifluoromethyl,
$R^2$ stands for hydrogen or halogen,
$R^3$ stands for halogen, trifluoromethyl, trifluoromethoxy, trifluoromethylthio or trifluoromethylsulphonyl,
$R^4$ stands for hydrogen or halogen,
X stands for nitrogen or the grouping C—$R^5$,
in which
$R^5$ stands for hydrogen or halogen,
A stands for optionally branched alkanediyl and
Z stands for cyano or the grouping —CO—Y,
wherein
Y stands for halogen, hydroxyl, amino, alkylamino, alkenylamino, alkinylamino, arylamino, aralkylamino, alkoxycarbonylalkylamino, cyanamino, dialkylamino, dialkenylamino, alkylsulphonylamino, arylsulphonylamino, hydroxyamino, alkoxyamino, hydrazino, alkylsulphonylhydrazino, arylsulphonylhydrazino, alkylthio, arylthio, aralkylthio, alkoxycarbonylalkylthio or for the grouping —O—$R^6$,
wherein
$R^6$ stands for an optionally halogen-substituted radical from the series alkyl, alkenyl, alkinyl, alkoxyalkyl, alkylthioalkyl, alkylsulphinylalkyl, alkylsulphonylalkyl, aryloxyalkyl, arylthioalkyl, arylalkoxyalkyl, arylalkylthioalkyl, trialkylsilylalkyl, alkoxycarbonylalkyl, alkylaminocarbonylalkyl, arylaminocarbonylalkyl, N-alkyl-N-aryl-aminocarbonylalkyl, aralkyl, azolylalkyl and alkylideneamino, or for an ammonium, alkylammonium, alkali metal or alkaline earth metal equivalent, or for the grouping

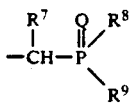

wherein
$R^7$ stands for hydrogen, alkyl, aryl, furyl, thienyl or pyridyl,
$R^8$ stands for alkyl or alkoxy,
$R^9$ stands for alkoxy and
Q stands for oxygen or sulphur, or
$R^6$ furthermore stands for the grouping —$(CH_2)_n$—$R^{10}$,
wherein
$R^{10}$ stands for an optionally halogen- and/or alkyl-substituted heterocyclic radical from the series furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl or pyrimidinyl, and
n stands for the numbers 0, 1 or 2,
have now been found.

In the event that the new (6-(hetero)aryloxy-naphthalen-2-yl-oxy)-alkanecarboxylic acid derivatives contain asymmetric carbon atoms, the invention relates to both the individual isomers possible and mixtures of these isomers.

Furthermore, it has been found that the new (6-(hetero)-aryloxy-naphthalen-2-yl-oxy)-alkanecarboxylic acid derivatives of the formula (I) are obtained when (a) 6-(hetero)aryloxy-2-naphthols of the general formula (II)

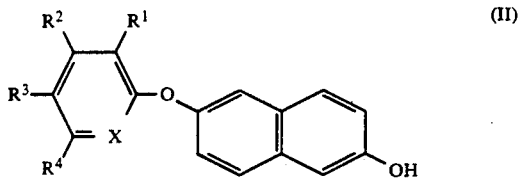

in which
$R^1$, $R^2$, $R^3$, $R^4$ and X have the abovementioned meanings,
are reacted with carboxylic acid derivatives of the general formula (III)

$$Z^1\text{—A—Z} \qquad (III)$$

in which
A and Z have the abovementioned meanings and
$Z^1$ stands for a nucleophilic leaving group,
if appropriate in the presence of an acid acceptor and if appropriate in the presence of a diluent, or (b) halogeno-(hetero)aryl compounds of the general formula (IV)

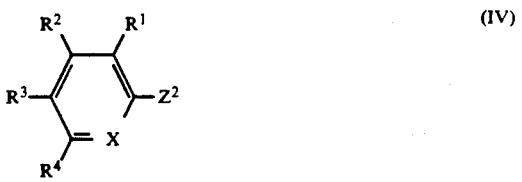

in which
$R^1$, $R^2$, $R^3$, $R^4$ and X have the abovementioned meanings and
$Z^2$ stands for halogen,
are reacted with (6-hydroxy-naphthalen-2-yl-oxy)-alkanecarboxylic acid derivatives of the general formula (V)

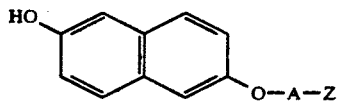

in which

A and Z have the abovementioned meanings, if appropriate in the presence of an acid acceptor and if appropriate in the presence of a diluent, or (c) in the event that, in formula (I), Z stands for the grouping —CO—Y, wherein Y stands for hydroxyl and A, $R^1$, $R^2$, $R^3$, $R^4$ and X have the abovementioned meanings, compounds of the formula (I) in which Z stands for cyano or for the grouping —CO—Y, wherein Y stands for methoxy or ethoxy and A, $R^1$, $R^2$, $R^3$, $R^4$ and Y have the abovementioned meanings, are reacted with an alkali metal hydroxide in the presence of an organic solvent, the reaction mixture is concentrated, if appropriate, and then acidified with a mineral acid, or (d) in the event that, in formula (I), Z stands for the grouping —CO—Y, wherein Y stands for halogen and A, $R^1$, $R^2$, $R^3$, $R^4$ and X have the abovementioned meanings, compounds of the general formula (I) in which Z stands for the grouping —CO—Y, wherein Y stands for hydroxyl and A, $R^1$, $R^2$, $R^3$, $R^4$ and X have the abovementioned meanings, are reacted with a halogenating agent, if appropriate in the presence of a diluent and if appropriate in the presence of a catalyst, or (e) in the event that, in formula (I), Z stands for the grouping —CO—Y, wherein Y has the meaning given above with the exception of halogen and A, $R^1$, $R^2$, $R^3$, $R^4$ and X have the abovementioned meanings, compounds of the general formula (I) in which Z stands for the grouping —CO—Y, wherein Y stands for halogen and A, $R^1$, $R^2$, $R^3$, $R^4$ and X have the abovementioned meanings, are reacted with compounds of the general formula (VI)

$$H-Y \quad (VI)$$

in which

Y has the meaning given above with the exception of halogen, if appropriate in the presence of an acid acceptor and if appropriate in the presence of a diluent, or (f) in the event that, in formula (I), Z stands for the grouping —CO—Y, wherein Y stands for the grouping —O—$R^6$, wherein $R^6$ has the abovementioned meaning with the exception of ammonium, alkylammonium, alkali metal and alkaline earth metal, and A, $R^1$, $R^2$, $R^3$, $R^4$ and X have the abovementioned meanings, compounds of the general formula (I) in which Z stands for the grouping —CO—Y, wherein Y stands for hydroxyl and A, $R^1$, $R^2$, $R^3$, $R^4$ and Y have the abovementioned meanings, are reacted with compounds of the general formula (VII)

$$Z^3-R^{6-1} \quad (VII)$$

in which $R^{6-1}$ has the meaning given above for $R^6$, with the exception of ammonium, alkylammonium, alkali metal and alkaline earth metal, and $Z^3$ stands for halogen, if appropriate in the presence of an acid acceptor and if appropriate in the presence of a diluent, or (g) in the event that, in formula (I), Z stands for the grouping —CO—Y, wherein Y stands for the grouping —O—$R^6$, wherein $R^6$ has the abovementioned meaning, with the exception of ammonium, alkylammonium, alkali metal and alkaline earth metal, and A, $R^1$, $R^2$, $R^3$, $R^4$ and X have the abovementioned meanings, compounds of the formula (I) in which Z stands for cyano and A, $R^1$, $R^2$, $R^3$ and $R^4$ have the abovementioned meanings, are reacted with hydroxyl compounds of the general formula (VIII)

$$HO-R^{6-2} \quad (VIII)$$

in which $R^{6-2}$ stands for $C_1$–$C_6$-alkyl, $C_3$–$C_4$-alkenyl, $C_3$–$C_4$-alkinyl, $C_1$–$C_4$-alkoxy-$C_1$–$C_4$-alkyl, $C_1$–$C_4$-alkylthio-$C_1$–$C_4$-alkyl, phenoxy-$C_1$–$C_3$-alkyl, phenylthio-$C_1$–$C_3$-alkyl, benzyloxy-$C_1$–$C_3$-alkyl, benzylthio-$C_1$–$C_3$-alkyl and $C_1$–$C_4$-alkoxycarbonyl-$C_1$–$C_2$-alkyl, in the presence of a mineral acid and if appropriate in the presence of a diluent.

Finally, it has been found that the new (6-(hetero)aryloxy-naphthalen-2-yl-oxy)-alkanecarboxylic acid derivatives of the general formula (I) exhibit powerful herbicidal properties.

Surprisingly, the (6-(hetero)aryloxy-naphthalen-2-yl-oxy)-alkanecarboxylic acid derivatives, according to the invention, of the formula (I) show a considerably better action against problem weeds than methyl α-(4-(2,4-dichlorophenoxy)-phenoxy)-propionate, which is a structurally similar previously known active compound of the same type of action, while being well tolerated by important crop plants.

Preferably, the invention relates to compounds of the formula (I) in which $R^1$ stands for hydrogen, fluorine, chlorine, bromine, cyano or trifluoromethyl, $R^2$ stands for hydrogen, fluorine or chlorine, $R^3$ stands for fluorine, chlorine, bromine, trifluoromethyl, trifluoromethoxy, trifluoromethylthio or trifluoromethylsulphonyl, $R^4$ stands for hydrogen, fluorine or chlorine, X stands for nitrogen or the grouping C-$R^5$, wherein $R^5$ stands for hydrogen, fluorine, chlorine or bromine, A stands for optionally branched $C_1$–$C_4$-alkanediyl and Z stands for cyano or the grouping —CO—Y, wherein Y stands for chlorine, hydroxyl, amino, $C_1$–$C_6$-alkylamino, $C_3$–$C_4$-alkenylamino, $C_3$–$C_4$-alkinylamino, phenylamino, benzylamino, $C_1$–$C_4$-alkoxycarbonyl-$C_1$–$C_2$-alkylamino, cyanamino, di-($C_1$–$C_4$-alkyl)-amino, di-($C_3$–$C_4$-alkenyl)-amino, $C_1$–$C_4$-alkylsulphonylamino, phenylsulphonylamino, tolylsulphonylamino, hydroxyamino, $C_1$–$C_6$-alkoxyamino, hydrazino, $C_1$–$C_4$-alkylsulphonylhydrazino, phenylsulphonylhydrazino, tolylsulphonylhydrazino, $C_1$–$C_4$-alkylthio, phenylthio, benzylthio, $C_1$–$C_4$-alkoxy-carbonyl-$C_1$–$C_2$-alkylthio, or for the grouping —O—$R^6$, wherein $R^6$ stands for an optionally fluorine- and/or chlorine-substituted radical from the series comprising $C_1$–$C_6$-alkyl, $C_3$–$C_4$-alkenyl, $C_3$–$C_4$-alkinyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulphinyl-$C_1$–$C_4$-alkyl, $C_1$–$C_4$-alkylsulphonyl-$C_1$–$C_4$-alkyl, phenoxy-$C_1$–$C_3$-alkyl, trimethylsilylmethyl, phenylthio-$C_1$–$C_3$-alkyl, benzyloxy-$C_1$–$C_3$-alkyl, benzylthio-$C_1$–$C_3$-alkyl, $C_1$–$C_4$-alkoxy-carbonyl-$C_1$–$C_2$-alkyl, $C_1$–$C_4$-alkylamino-carbonyl-$C_1$–$C_2$-alkyl, phenylaminocarbonyl-$C_1$–$C_4$-alkyl, N-($C_1$–$C_4$-alkyl)-

N-phenyl-aminocarbonyl-$C_1$–$C_4$-alkyl, benzyl, pyrazolyl-$C_1$–$C_4$-alkyl and $C_2$–$C_4$-alkylideneamino, or for an ammonium, a $C_1$–$C_4$-alkylammonium, a sodium, potassium or calcium equivalent, or for the grouping

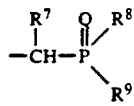

wherein $R^7$ stands for hydrogen, $C_1$–$C_4$-alkyl, phenyl, furyl, thienyl or pyridyl, $R^8$ stands for $C_1$–$C_4$-alkyl or $C_1$–$C_4$-alkoxy, $R^9$ stands for $C_1$–$C_4$-alkoxy and Q stands for oxygen or sulphur, or $R^6$ furthermore stands for the grouping —$(CH_2)_n$—$R^{10}$, wherein n stands for the numbers 0, 1 or 2 and $R^{10}$ stands for an optionally fluorine-, chlorinebromine- and/or $C_1$–$C_4$-alkyl-substituted heterocyclic radical from the series furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl or pyrimidinyl, and to their optically active isomers.

In particular, the invention relates to compounds of the formula (I) in which $R^1$ stands for cyano, fluorine or chlorine, $R^2$ stands for hydrogen, fluorine or chlorine, $R^3$ stands for chlorine or trifluoromethyl, $R^4$ stands for hydrogen, fluorine or chlorine, X stands for nitrogen or the grouping C—$R^5$, wherein $R^5$ stands for hydrogen, fluorine or chlorine, A stands for methylene (—$CH_2$—), dimethylene (—$CH_2CH_2$—), trimethylene (—$CH_2$—)$_3$ or ethylidene

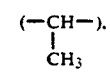

and

Z stands for cyano or the grouping —CO—Y, wherein

Y stands for chlorine, hydroxyl, amino, $C_1$–$C_4$-alkylamino, phenylamino, $C_1$–$C_4$-alkoxy-carbonyl-$C_1$–$C_2$-alkylamino, di-($C_1$–$C_3$-alkyl)-amino, diallylamino, $C_1$–$C_4$-alkylsulphonylamino, phenylsulphonylamino, hydroxyamino, cyanamino, $C_1$–$C_4$-alkoxyamino, hydrazino, $C_1$–$C_4$-alkylsulphonylhydrazino, phenylsulphonylhydrazino, $C_1$–$C_4$-alkylthio or $C_1$–$C_4$-alkoxy-carbonyl-$C_1$–$C_2$-alkylthio, or for the grouping —O—$R^6$, wherein $R^6$ stands for $C_1$–$C_4$-alkyl, $C_1$–$C_2$-alkoxy-$C_1$–$C_2$-alkyl, $C_1$–$C_2$-alkylthio-$C_1$–$C_2$-alkyl, $C_1$–$C_2$-alkylsulphinyl-$C_1$–$C_2$-alkyl, $C_1$–$C_2$-alkylsulphonyl-$C_1$–$C_2$-alkyl, benzyloxy-$C_1$–$C_3$-alkyl, benzylthio-$C_1$–$C_3$-alkyl, $C_1$–$C_4$-alkoxycarbonyl-$C_1$–$C_2$-alkyl, $C_1$–$C_4$-alkylaminocarbonyl-$C_1$–$C_2$-alkyl, benzyl and trimethylsilylmethyl, or for an ammonium, $C_1$–$C_3$-alkylammonium, sodium or potassium equivalent, or for the grouping

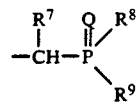

wherein $R^7$ stands for hydrogen, methyl, phenyl, furyl, thienyl or pyridyl, $R^8$ stands for methoxy or ethoxy, $R^9$ stands for methoxy or ethoxy and Q stands for oxygen or sulphur, or $R^6$ furthermore stands for the grouping (—$CH_2$—)$_n R^{10}$, wherein n stands for the numbers 0, 1 or 2 and $R^{10}$ stands for an optionally chlorine- and/or methyl-substituted heterocyclic radical from the series furyl, tetrahydrofuryl, thienyl, perhydropyranyl, oxazolyl, thiazolyl and dioxolanyl, and to their optically active isomers.

In case the compounds of the formula (I) conlain an optically active centre, the R-enantiomers of the possible isomers are especially preferred.

If, for example, 6-(3,5-dichloro-pyridin-2-yl-oxy)-2-naphthol and ethyl α-bromo-propionate are used as starting substances for process (a) according to the invention, the course of reaction may be represented by the following equation:

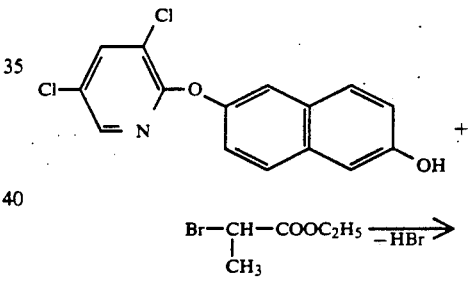

If, for example, 3,4,5-trichloro-benzotrifluoride and butyl (6-hydroxy-naphthalen-2-yl-oxy)-acetate are used as starting substances for process (b) according to the invention, the course of reaction may be represented by the following equation:

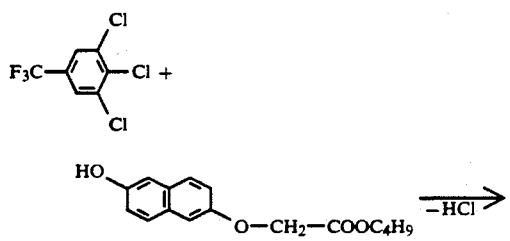

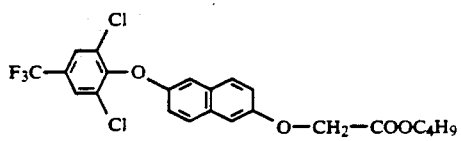

If, for example, methyl β-(6-(2-chloro-4-trifluoromethylphenoxy)-naphthalen-2-yl-oxy)-propionate and sodium hydroxide solution are used as starting substances for process (c) according to the invention, the course of reaction may be represented by the following equation:

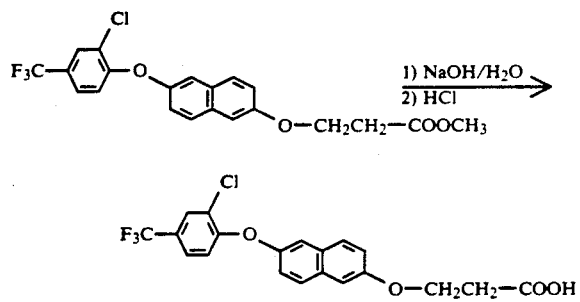

If, for example, α-(6-(2,6-dichloro-3-fluoro-4-trifluoromethyl-phenoxy)-naphthalen-2-yl-oxy)-propionic acid and thionyl chloride are used as starting substances for process (d) according to the invention, the course of reaction may be represented by the following equation:

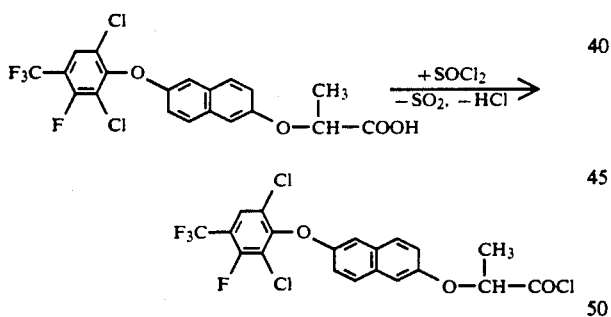

If, for example, α-(6-(2-chloro-6-fluoro-4-trifluoromethyl-phenoxy)-naphthalen-2-yl-oxy)-propionic chloride and methyl mercaptoacetate are used as starting substances for process (e) according to the invention, the course of reaction may be represented by the following equation:

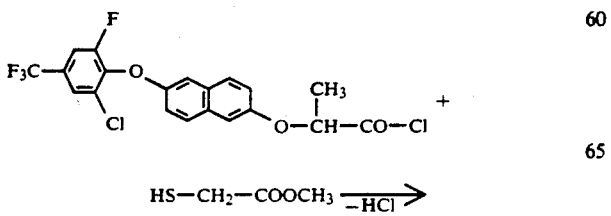

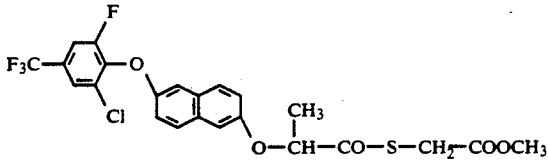

If, for example, (6-(2,3,6-trichloro-4-trifluoromethylphenoxy)-naphthalen-2-yl-oxy)-acetic acid and trimethylsilylmethyl chloride are used as starting substances for process (f) according to the invention, the course of reaction may be represented by the following equation:

If, for example, (6-(2-chloro-6-fluoro-4-trifluoromethylphenoxy)-naphthalen-2-yl-oxy)-acetonitrile and methanol are used as starting substances for process (g) according to the invention, the course of reaction may be represented by the following equation:

Formula (II) provides a general definition for the 6-(hetero)aryloxy-2-naphthols to be used as starting substances for the preparation of compounds of the formula (I) in process (a) according to the invention.

In formula (II), $R^1$, $R^2$, $R^3$, $R^4$ and X preferably, or in particular, have those meanings which have already been indicated above in connection with the description of the compounds of the formula (I) according to the invention as being preferred, or particularly preferred, for $R^1$, $R^2$, $R^3$, $R^4$ and X.

Examples of the starting substances of the formula (II) which may be mentioned are: 6-(4-trifluoromethylphenoxy)-2-naphthol, 6-(2-chloro-4-trifluoromethylphenoxy)-2-naphthol, 6-(2,6-dichloro-4-trifluoromethyl-phenoxy)-2-naphthol, 6-(2-chloro-6-fluoro-4-trifluoromethyl-phenoxy)-2-naphthol, 6-(2,6-dichloro-3- fluoro-4-trifluoromethyl-phenoxy)-2-naphthol, 6-(2,3,6-trichloro-4-trifluoromethyl-phenoxy)-2-naphthol and 6-(3,5-dichloropyridin-2-yl-oxy)-2-naphthol.

The starting substances of the formula (II) are not known hitherto from the literature. The compounds of the formula (II) are obtained, when corresponding halogeno(hetero)aryl compounds of the general formula (IV)

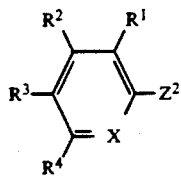

in which
R¹, R², R³, R⁴, X and Z² have the abovementioned meanings,
are reacted with 2,6-dihydroxynaphthalene in the presence of an acid acceptor, such as, for example, sodium hydroxide or potassium hydroxide, and in the presence of a diluent, such as, for example, dimethylformamide, dimethylacetamide, dimethyl sulphoxide, tetramethylenesulphone or N-methyl-pyrrolidone, at temperatures between 20° C. and 150° C., and the reaction product is worked up by customary methods.

Formula (IV) provides a general definition of the halogeno-(hetero)aryl compounds. In formula (IV), R¹, R², R³, R⁴ and X preferably, or in particular, have those meanings which have already been mentioned in connection with the description of the compounds of the formula (I) according to the invention as being preferred, or particularly preferred, for R¹, R², R³, R⁴ and X, and Z² preferably stands for chlorine or fluorine.

Examples of the halogeno-(hetero)aryl compounds of the formula (IV) which may be mentioned are: 4-chlorobenzotrifluoride, 3,4-dichloro-benzotrifluoride, 3,4,5-trichloro-benzotrifluoride, 3,4-dichloro-5-fluorobenzotrifluoride, 2,3,4,5-tetrachloro-benzotrifluoride, 3,5-dichloro-2,4-difluoro-benzotrifluoride, 3-chloro-4,5-difluoro-benzotrifluoride and 2,3,5-trichloro-pyridine.

The compounds of the formula (IV) are known and/or can be prepared by methods known per se (cf. J. Chem. Soc. 1969, 211-217; loc. cit. 1971, 1547-1549; EP-A 34,402; U.S. Pat. No. 4,424,396; EP-A 145,314; FR-A 2,538,380 (Chem. Abstracts 102 (1985), 61914x)).

Formula (III) provides a general definition of the carboxylic acid derivatives to be further employed as starting substances in process (a) according to the invention. In formula (III), A and Z preferably, or in particular, have those meanings which have already been mentioned above in connection with the description of the compounds of the formula (I) according to the invention as being preferred, or particularly preferred, and Z¹ preferably stands for chlorine, bromine, iodine, optionally fluorine- or chlorine-substituted C₁-C₄-alkylsulphonyloxy or optionally fluorine-, chlorine-, bromine- or methyl-substituted phenylsulphonyloxy, in particular for chlorine, bromine, methylsulphonyloxy, phenylsulphonyloxy or 4-methylphenylsulphonyloxy.

Examples of the compounds of the formula (III) which may be mentioned are: chloroacetonitrile, bromoacetonitrile, β-bromo-propionitrile, β-chloropropionitrile, the methyl esters, ethyl esters, propyl esters, isopropyl esters, butyl esters, isobutyl esters and secbutyl esters of α-chloropropionic acid, α-bromopropionic acid and α-iodopropionic acid, the methyl esters, ethyl esters, propyl esters, isopropyl esters, butyl esters, isobutyl esters and sec-butyl esters of β-chloropropionic acid, β-bromopropionic acid and β-iodopropionic acid, the methyl esters, ethyl esters, propyl esters, isopropyl esters, butyl esters, isobutyl esters and sec-butyl esters of chloroacetic acid, bromoacetic acid and iodoacetic acid, the methyl esters, ethyl esters, propyl esters, butyl esters, isopropyl esters, isobutyl esters and sec-butyl esters of α-methylsulphonyloxypropionic acid, α-ethylsulphonyloxypropionic acid, α-propylsulphonyloxypropionic acid, α-butylsulphonyloxypropionic acid, α-trifluoromethylsulphonyloxypropionic acid, α-phenylsulphonyloxypropionic acid and α-(4-methylphenylsulphonyloxy)-propionic acid.

The starting substances of the formula (III) are known and/or can be prepared by methods known per se (cf. DE-OS (German Published Specification) 2,758,002, DE-OS (German Published Specification) 2,854,542).

Process (a) according to the invention for the preparation of the new compounds of the formula (I) is preferably carried out using diluents. Suitable diluents in this process are virtually all the inert organic solvents. These include preferably aliphatic and aromatic hydrocarbons, optionally halogenated, such as pentane, hexane, heptane, cyclohexane, petroleum ether, benzine, naphtha, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, dimethyl sulphoxide, tetramethylene sulphone and hexamethylphosphoric triamide.

Acid acceptors which can be employed in process (a) according to the invention are all acid-binding agents which can customarily be employed for such reactions. Preferably suitable are alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate, potassium carbonate, sodium tert-butylate and potassium tertbutylate, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (a) according to the invention, the reaction temperatures may be varied within a relatively wide range. In general, the process is carried out at temperatures between 0° C. and 150° C., preferably at temperatures between 20° C. and 100° C.

Process (a) according to the invention is generally carried out under atmospheric pressure. However, it is also possible for the process to be carried out under increased or reduced pressure.

For carrying out the process (a) according to the invention, 0.5 to 1.2 moles, preferably 0.7 to 1.0 mole, of carboxylic acid derivative of the formula (III) is generally employed per mole of 6-(hetero)aryloxy-2-naphthol of the formula (II). Generally, the reaction components are mixed together at room temperature or with slight cooling, and the mixture is then stirred until the reaction is complete, if desired, at increased temperature.

Working up can be carried out in a customary manner. For example, the reaction mixture is stirred or shaken with an acid, such as, for example, hydrochloric acid or sulphuric acid and water, and with a virtually water-immiscible organic solvent, such as, for example, dichloromethane or toluene, the organic phase is separated off, washed with water, dried and filtered. The filtrate is concentrated, and the product of the formula (I) remaining in the residue can be purified in a customary manner, for example by column chromatography.

The halogenoheteroaryl compounds to be used as starting substances in process (b) according to the invention have already been described above.

Formula (V) provides a general definition of the (6-hydroxy-naphthalen-2-yl-oxy)-alkanecarboxylic acid derivatives further to be employed as starting substances in process (b) according to the invention. In formula (VI) A and Z preferably, or in particular, have those meanings which have already been mentioned above in connection with the description of the compounds of the formula (I) according to the invention as being preferred, or particularly preferred.

Examples of the starting substances of the formula (V) which may be mentioned are: the nitriles, methyl esters, ethyl esters, propyl esters, isopropyl esters, butyl esters, isobutyl esters and sec-butyl esters of $\alpha$-(6-hydroxy-naphthalen-2-yl-oxy)-propionic acid, the nitriles, methyl esters, ethyl esters, propyl esters, isopropyl esters, butyl esters, isobutyl esters and sec-butyl esters of $\beta$-(6-hydroxy-naphthalen-2-yl-oxy)-propionic acid, and the nitriles, methyl esters, ethyl esters, propyl esters, isopropyl esters, butyl esters, isobutyl esters and sec-butyl esters of (6-hydroxy-naphthalen-2-yl-oxy)-acetic acid.

The starting substances of the formula (V) are known and/or can be prepared by methods known per se (cf. U.S. Pat. No. 3,740,437).

Process (b) is preferably carried out using a diluent. Suitable diluents are mainly those which have already been mentioned in the description of process (a) according to the invention. Particularly preferred solvents are aprotic polar organic solvents, such as, for example, acetone, acetonitrile, methyl ethyl ketone, propionitrile, dimethylformamide, dimethylacetamide, dimethyl sulphoxide, sulpholane and N-methylpyrrolidone.

Process (b) is preferably carried out in the presence of an acid acceptor. Suitable acid acceptors are mainly those which have already been mentioned in the description of process (a) according to the invention.

When carrying out process (b) according to the invention the reaction temperatures may be varied within a relatively wide range. In general, the process is carried out at temperatures between 0° C. and 200° C., preferably at temperatures between 20° C. and 150° C.

Process (b) according to the invention is generally carried out under atmospheric pressure. However, it is also possible for the process to be carried out under increased or reduced pressure.

For carrying out process (b) according to the invention, 0.5 to 2 moles, preferably 0.7 to 1.5 moles, of (6-hydroxy-naphthalen-2-yl-oxy)-alkanecarboxylic acid derivative of the formula (V) is generally employed per mole of halogeno-(hetero)aryl compound of the formula (IV).

The reaction and working up can be carried out as described above for process (a).

Formula (I) provides a general definition of the compounds to be employed as starting substances in process (c) according to the invention, with the proviso that Z stands for cyano or the grouping —CO—Y, wherein Y stands for methoxy or ethoxy. In this case, A, $R^1$, $R^2$, $R^3$, $R^4$ and X preferably, or in particular, have those meanings which have already been mentioned above in the context of the description of the compounds of the formula (I) according to the invention as being preferred, or particularly preferred.

Examples of the starting substances for process (c) which may be mentioned are: the nitriles, methyl esters and ethyl esters of $\alpha$-(6-(3,5-dichloro-pyridin-2-yl-oxy)-, $\alpha$-(6-(4-trifluoromethyl-phenoxy)-, $\alpha$-(6-(2-chloro-4-trifluoromethyl-phenoxy)-, $\alpha$-(6-(2,6-dichloro-4-trifluoromethyl-phenoxy)-, $\alpha$-(6-(2-chloro-6-fluoro-4-trifluoromethyl-phenoxy)-, $\alpha$-(6-(2,3,6-trichloro-4-trifluoromethyl-phenoxy)- and $\alpha$-(6-(2,6-dichloro-3-fluoro-4-trifluoromethyl-phenoxy)-naphthalen-2-yl-oxy)-propionic acid; the nitriles, methyl esters and ethyl esters of $\beta$-(6-(3,5-dichloro-pyridin-2-yl-oxy)-, $\beta$-(6-(4-trifluoromethyl-phenoxy)-, $\beta$-(6-(2-chloro-4-trifluoromethyl-phenoxy)-, $\beta$-(6-(2,6-dichloro-4-trifluoromethyl-phenoxy)-, $\beta$-(6-(2-chloro-6-fluoro-4-trifluoromethyl-phenoxy)-, $\beta$-(6-(2,3,6-trichloro-4-trifluoromethyl-phenoxy)- and $\beta$-(6-(2,6-dichloro-3-fluoro-4-trifluoromethyl-phenoxy)-naphthalen-2-yl-oxy)-propionic acid; the nitriles, methyl esters and ethyl esters of (6-(3,5-dichloro-pyridin-2-yl-oxy)-, (6-(4-trifluoromethyl-phenoxy)-, (6-(2-chloro-4-trifluoromethyl-phenoxy)-, (6-(2,6-dichloro-4-trifluoromethyl-phenoxy)-, (6-(2-chloro-6-fluoro-4-trifluoromethyl-phenoxy)-, (6-(2,3,6-trichloro-4-trifluoromethyl-phenoxy)- and (6-(2,6-dichloro-3-fluoro-4-trifluoromethyl-phenoxy)-naphthalen-2-yl-oxy)-acetic acid.

The abovementioned starting substances of the formula (I) for process (c) are new compounds according to the invention; they can be prepared by process (a) or (b) according to the invention.

Process (c) is carried out using alkali metal hydroxides. Examples which may be mentioned in this context are lithium hydroxide, sodium hydroxide and potassium hydroxide. Preferably, sodium hydroxide is used.

Process (c) is carried out in the presence of water and if appropriate in the presence of an organic solvent. Organic solvents which are preferably employed are alcohols, such as, for example, methanol or ethanol.

For acidifying, the customary mineral acids, such as, for example, hydrochloric acid or sulphuric acid, are used in process (c).

When carrying out process (c) according to the invention, the reaction temperatures may be varied within a relatively wide range. In general, the process is carried out at temperatures between 10° C. and 150° C., preferably at temperatures between 20° C. and 100° C.

Process (c) according to the invention is generally carried out under atmospheric pressure. However, it is also possible for the process to be carried out under increased or reduced pressure.

For carrying out process (c), 0.1 to 10 moles, preferably 0.5 to 2 moles, of alkali metal hydroxide are generally employed per mole of starting compound of the formula (I). In general, the reaction components are mixed together at room temperature and the reaction mixture is stirred until the reaction is complete, if appropriate at an increased temperature. If necessary, the reaction mixture is concentrated, cooled and acidified, and the reaction product which is in the form of crystals can be isolated by filtering with suction.

Formula (I) provides a general definition of the compounds to be employed as starting substances in process (d) according to the invention, with the proviso that Z stands for the grouping —CO—Y, wherein Y stands for hydroxyl. In this case, A, $R^1$, $R^2$, $R^3$, $R^4$ and X preferably, or particularly, have those meanings which have already been mentioned above in the context of the description of the compounds of the formula (I) according to the invention as being preferred, or particularly preferred.

Examples of the starting substances in process (d) which may be mentioned are: α-(6-(3,5-dichloropyridin-2-yl-oxy)-, α-(6-(4-trifluoromethyl-phenoxy)-, α-(6-(2-chloro-4-trifluoromethyl-phenoxy)-, α-(6-(2,6-dichloro-4-trifluoromethyl-phenoxy)-, α-(6-(2-chloro-6-fluoro-4-trifluoromethyl-phenoxy)-, α-(6-(2,3,6-trichloro-4-trifluoromethyl-phenoxy)- and α-(6-(2,6-dichloro-3-fluoro-4-trifluoromethyl-phenoxy)-naphthalen-2-yl-oxy)-propionic acid; β-(6-(3,5-dichloro-pyridin-2-yl-oxy)-, β-(6-(4-trifluoromethyl-phenoxy)-, β-(6-(2-chloro-4-trifluoromethyl-phenoxy)-, β-(6-(2,6-dichloro-4-trifluoromethyl-phenoxy)-, β-(6-(2-chloro-6-fluoro-4-trifluoromethyl-phenoxy)-, β-(6-(2,3,6-trichloro-4-trifluoromethyl-phenoxy)- and β-(6-(2,6-dichloro-3-fluoro-4-trifluoromethyl-phenoxy)-naphthalen-2-yl-oxy)-propionic acid; (6-(3,5-dichloro-pyridin-2-yl-oxy)-, (6-(4-trifluorometryl-phenoxy)-, (6-(2-chloro-4-trifluoromethylphenoxy)-, (6-(2,6-dichloro-4-trifluoromethyl-phenoxy)-, (6-(2-chloro-6-fluoro-4-trifluoromethyl-phenoxy)-, (6-(2,3,6-trichloro-4-trifluoromethyl-phenoxy)- and (6-(2,6-dichloro-3-fluoro-4-trifluoromethyl-phenoxy)-naphthalen-2-yl-oxy)-acetic acid.

The abovementioned starting substances of the formula (I) for process (d) are new compounds according to the invention; they can be prepared by process (c) according to the invention.

Process (d) is carried out using a halogenating agent. It is possible to employ the customary agents for converting carboxylic acids to carboxylic halides. In this context, examples which may be mentioned are phosgene, thionyl chloride, phosphoryl chloride and benzotrichloride. Preferably, thionyl chloride is used as the halogenating agent.

If necessary, process (d) is carried out in the presence of a catalyst. It is possible to use the catalysts customary for the preparation of acid chlorides from acids, such as, for example, pyridine or dimethylformamide.

Process (d) is optionally carried out in the presence of a diluent. Preferred solvents which may be considered are inert organic solvents from the series of the halogenated hydrocarbons, such as, for example, dichloromethane, chloroform, tetrachloromethane or 1,2-dichloroethane.

When carrying out process (d) according to the invention, the reaction temperatures may be varied within a relatively wide range. In general, the process is carried out at temperatures between 0° C. and 100° C., preferably at temperatures between 10° C. and 90° C.

Process (d) is generally carried out under atmospheric pressure.

For carrying out process (d), 1 to 100 moles, preferably 2 to 50 moles, of halogenating agent are generally employed per mole of starting substance of the formula (I). In general, the reaction components are mixed together at room temperature, and the reaction mixture is stirred until the reaction is complete, if appropriate, at an increased temperature. The volatile components are distilled off under reduced pressure, and the reaction product remaining can be purified in a customary manner, but can also be employed in further reactions without further purification.

Formula (I) provides a general definition of the compounds to be used as starting substances in process (e) according to the invention, with the proviso that Z stands for the grouping —CO—Y, wherein Y stands for halogen. In this case, A, $R^1$, $R^2$, $R^3$, $R^4$ and X preferably, or in particular, have those meanings which have already been mentioned above in the context of the description of the compounds of the formula (I) according to the invention as being preferred, or particularly preferred, and Y preferably stands for fluorine, chlorine or bromine, in particular for chlorine.

Examples of the starting substances in process (e) which may be mentioned are: α-(6-(3,5-dichloropyridin-2-yl-oxy)-, α-(6-(4-trifluoromethyl-phenoxy)-, α-(6-(2-chloro-4-trifluoromethyl-phenoxy)-, α-(6-(2,6-dichloro-4-trifluoromethyl-phenoxy)-, α-(6-(2-chloro-6-fluoro-4-trifluoromethyl-phenoxy)-, α-(6-(2,3,6-trichloro-4-trifluoromethyl-phenoxy)- and α-(6-(2,6-dichloro-3-fluoro-4-trifluoromethyl-phenoxy)-naphthalen-2-yl-oxy)-propionic chloride; β-(6-(3,5-dichloro-pyridin-2-yl-oxy)-, β-(6-(4-trifluoromethyl-phenoxy)-, β-(6-(2-chloro-4-trifluoromethyl-phenoxy)-, β-(6-(2,6-dichloro-4-trifluoromethyl-phenoxy)-, β-(6-(2-chloro-6-fluoro-4-trifluoromethyl-phenoxy)-, β-(6-(2,3,6-trichloro-4-trifluoromethyl-phenoxy)- and β-(6-(2,6-dichloro-3-fluoro-4-trifluoromethyl-phenoxy)-naphthalen-2-yl-oxy)-propionic chloride; (6-(3,5-dichloro-pyridin-2-yl-oxy)-, (6-(4-trifluoromethyl-phenoxy)-, (6-(2-chloro-4-trifluoromethylphenoxy)-, (6-(2,6-dichloro-4-trifluoromethyl-phenoxy)-, (6-(2-chloro-6-fluoro-4-trifluoromethyl-phenoxy)-, (6-(2,3,6-trichloro-4-trifluoromethyl-phenoxy)- and (6-(2,6-dichloro-3-fluoro-4-trifluoromethyl-phenoxy)-naphthalen-2-yl-oxy)-acetic chloride.

The abovementioned starting substances of the formula (I) for process (e) are new compounds according to the invention; they can be prepared by process (d) according to the invention.

Formula (VI) provides a general definition of the compounds further to be employed as starting substances in process (e) according to the invention. In formula (VI), Y preferably, or in particular, has the meaning which has already been mentioned above in connection with the description of the compounds of the formula (I) according to the invention as being preferred, or particularly preferred, with the exception of halogen.

Examples of the starting substances of the formula (VI) which may be mentioned are: methylamine, ethylamine, propylamine, isopropylamine, aniline, cyanamide, dimethylamine, diethylamine, hydroxylamine, 0-methylhydroxylamine, hydrazine, methylsulphonylhydrazine, methanol, ethanol, propanol, isopropanol, butanol, isobutanol, sec-butanol, 2-methoxy-ethanol, 2-ethoxy-ethanol, 2-methylthio-ethanol, 2-ethylthioethanol, 2-benzyloxy-ethanol, 3-benzyloxy-propanol, 2-benzylthio-ethanol, diethyl and dimethyl hydroxymethanephosphonate, dimethyl and diethyl 1-hydroxyethane-phosphonate, dimethyl and diethyl 1-hydroxy-1-phenyl-methanephosphonate, acetoneoxime, 3-hydroxyfuran, furfuryl alcohol, perhydrofurfuryl alcohol, methyl and ethyl lactate, and methyl and ethyl glycollate.

These compounds are known chemicals for synthesis.

Process (e) is preferably carried out using a diluent. Suitable diluents are mainly those which have already been mentioned in the description of process (a) according to the invention.

Process (e) is preferably carried out in the presence of an acid acceptor. Suitable acid acceptors are mainly those which have already been mentioned in the description of process (a) according to the invention.

When carrying out process (e), the reaction temperatures may be varied within a relatively wide range. In general, the process is carried out at temperatures between $-20°$ C. and $+100°$ C., preferably at temperatures between 0° C. and 50° C.

Process (e) according to the invention is generally carried out under atmospheric pressure. However, it is also possible for the process to be carried out under increased or reduced pressure.

For carrying out process (e) according to the invention, the starting substances required in each case are generally employed in approximately equimolar amounts. However, it is also possible to employ one of the two components employed in each case in relatively large excess. The reactions are generally carried out in a suitable diluent in the presence of an acid acceptor, and the reaction mixture is stirred at the temperature specifically required for several hours.

In process (e) according to the invention, working up is carried out by customary methods. For example, the reaction mixture is concentrated, if required, and diluted with water, and the reaction product desired is extracted using a virtually water-immiscible organic solvent, for example, dichloromethane, chloroform, diethyl ether, toluene or xylene. The organic extraction solution is washed with water, dried with a customary drying agent, such as, for example, sodium sulphate, dried and filtered. The filtrate is concentrated, and the compounds of the formula (I) are obtained as crude products which can be purified in a customary manner, for example, by chromatography and/or by recrystallization.

Formula (I) provides a general definition of the compounds to be used as starting substances in process (f) according to the invention, with the proviso that Z stands for the grouping —CO—Y, wherein Y stands for hydroxyl. In this case, A, $R^1$, $R^2$, $R^3$, $R^4$ and X preferably, or in particular, have those meanings which have already been mentioned above in the context of the description of the compounds of the formula (I) according to the invention as being preferred, or particularly preferred.

Examples of the starting substances for process (f) which may be mentioned are: α-(6-(3,5-dichloropyridin-2-yl-oxy)-, α-(6-(4-trifluoromethyl-phenoxy)-, α-(6-(2-chloro-4-trifluoromethyl-phenoxy)-, α-(6-(2,6-dichloro-4-trifluoromethyl-phenoxy)-, α-(6-(2-chloro-6-fluoro-4-trifluoromethyl-phenoxy)-, α-(6-(2,3,6-trichloro-4-trifluoromethyl-phenoxy)- and α-(6-(2,6-dichloro-3-fluoro-4-trifluoromethyl-phenoxy)-naphthalen-2-yl-oxy)-propionic acid; β-(6-(3,5-dichloro-pyridin-2-yl-oxy)-, β-(6-(4-trifluoromethyl-phenoxy)-, β-(6-(2-chloro-4-trifluoromethyl-phenoxy)-, β-(6-(2,6-dichloro-4-trifluoromethyl-phenoxy)-, β-(6-(2-chloro-6-fluoro-4-trifluoromethyl-phenoxy)-, β-(6-(2,3,6-trichloro-4-trifluoromethyl-phenoxy)- and β-(6-(2,6-dichloro-3-fluoro-4-trifluoromethyl-phenoxy)-naphthalen-2-yl-oxy)-propionic acid; (6-(3,5-dichloro-pyridin-2-yl-oxy)-, (6-(4-trifluoromethyl-phenoxy)-, (6-(2-chloro-4-trifluoromethylphenoxy)-, (6-(2,6-dichloro-4-trifluoromethyl-phenoxy)-, (6-(2-chloro-6-fluoro-4-trifluoromethyl-phenoxy)-, (6-(2,3,6-trichloro-4-trifluoromethyl-phenoxy)- and (6-(2,6-dichloro-3-fluoro-4-trifluoromethyl-phenoxy)-naphthalen-2-yl-oxy)-acetic acid.

The abovementioned starting substances of the formula (I) for process (f) are new compounds according to the invention; they can be prepared by process (c) according to the invention.

Formula (VII) provides a general definition for the compounds further to be employed as starting substances in process (f) according to the invention. In formula (VII), $R^{6-1}$ preferably stands for $C_1$-$C_6$-alkyl, $C_3$-$C_4$-alkenyl, $C_3$-$C_4$-alkinyl, $C_1$-$C_4$-alkoxy-$C_1$-$C_4$-alkyl, $C_1$-$C_4$-alkylthio-$C_1$-$C_4$-alkyl, phenoxy-$C_1$-$C_3$-alkyl, trimethylsilylmethyl, phenylthio-$C_1$-$C_3$-alkyl, benzyloxy-$C_1$-$C_3$-alkyl, benzylthio-$C_1$-$C_3$-alkyl and $C_1$-$C_4$-alkoxy-carbonyl-$C_1$-$C_2$-alkyl, and $Z^3$ preferably stands for chlorine, bromine or iodine.

A particularly preferred starting compound of the formula (VII) for process (f) is trimethylsilylmethyl chloride.

The starting substances of the formula (VII) are known chemicals for synthesis.

Process (f) is preferably carried out using a diluent. Suitable diluents are mainly those which have already been mentioned in the description of process (a) according to the invention. Particularly preferred diluents are acetone, acetonitrile and dimethylformamide.

Process (f) is preferably carried out in the presence of an acid acceptor. Suitable acid acceptors are mainly those which have already been mentioned in the description of process (a) according to the invention. A particularly preferred acid acceptor is 1,8-diazabicyclo-[5.4.0]-undec-7-ene (DBU).

When carrying out process (f) according to the invention, the reaction temperatures can be varied within a relatively wide range. In general, the process is carried out at temperatures between 0° C. and 150° C., preferably at temperatures between 20° C. and 100° C.

Process (f) according to the invention is generally carried out under atmospheric pressure. However, it is also possible for the process to be carried out under increased or reduced pressure.

For carrying out process (f), 1 to 3 moles, preferably 1.1 to 2.5 moles, of starting substance of the formula (VII) are generally employed per mole of starting compound of the formula (I).

The reaction and working up can be carried out as described above for process (a).

Formula (I) provides a general definition of the compounds to be employed as starting substances in process (g) according to the invention with the proviso that Z stands for cyano. In this case, A, $R^1$, $R^2$, $R^3$, $R^4$ and X preferably, or in particular, have those meanings which have already been mentioned above in the context of the description of the compounds of the formula (I) according to the invention as being preferred, or particularly preferred.

Examples of the starting substances for process (g) which may be mentioned are: α-(6-(3,5-dichloropyridin-2-yl-oxy)-, α-(6-(4-trifluoromethyl-phenoxy)-, α-(6-(2-chloro-4-trifluoromethyl-phenoxy)-, α-(6-(2,6-dichloro-4-trifluoromehyl-phenoxy)-, α-(6-(2-chloro-6-fluoro-4-trifluoromethyl-phenoxy)-, α-(6-(2,3,6-trichloro-4-trifluoromethyl-phenoxy)- and α-(6-(2,6-dichloro-3-fluoro-4-trifluoromethyl-phenoxy)-naphthalen-2-yl-oxy)-propionitrile; β-(6-(3,5-dichloro-pyridin-2-yl-oxy)-, β-(6-(4-trifluoromethyl-phenoxy)-, β-(6-(2-chloro-4-trifluoromethyl-phenoxy)-, β-(6-(2,6-dichloro-4-trifluoromethyl-phenoxy)-, β-(6-(2-chloro-6-fluoro-4-trifluoromethyl-phenoxy)-, β-(6-(2,3,6-trichloro-4-trifluoromethyl-phenoxy)- and β-(6-(2,6-dichloro-3-fluoro-4-trifluoromethyl-phenoxy)-naphthalen-2-yl-oxy)-propionitrile; (6-(3,5-dichloro-pyridin-2-yl-oxy)-, (6-(4-trifluoromethyl-phenoxy)-, (6-(2-chloro-4-trifluoromethylphenoxy)-, (6-(2,6-dichloro-4-trifluoromethyl-phenoxy)-, (6-(2-chloro-6-fluoro-4-trifluoromethyl-phenoxy)-, (6-(2,3,6-trichloro-4-trifluoromethyl-phenoxy)- and (6-(2,6-dichloro- 3-fluoro-4-trifluoromethyl-phenoxy)-naphthalene 2-yl-oxy)-acetonitrile.

The abovementioned starting substances of the formula (I) for process (g) are new compounds according to the invention; they can be prepared by process (a) or (b) according to the invention.

Formula (VIII) provides a general definition of the compounds further to be employed as starting substances in process (g) according to the invention. In formula (VIII), $R^{6-2}$ preferably stands for $C_1$-$C_6$-alkyl, $C_3$-$C_4$-alkenyl, $C_3$-$C_4$-alkinyl, $C_1$-$C_4$-alkoxy-$C_1$-$C_4$-alkyl, $C_1$-$C_4$-alkylthio-$C_1$-$C_4$-alkyl, phenoxy-$C_1$-$C_3$-alkyl, phenylthio-$C_1$-$C_3$-alkyl, benzyloxy-$C_1$-$C_3$-alkyl, benzylthio-$C_1$-$C_3$-alkyl and $C_1$-$C_4$-alkoxycarbonyl-$C_1$-$C_2$-alkyl.

In formula (VIII), $R^{6-2}$ particularly stands for $C_1$-$C_4$-alkyl, $C_1$-$C_2$-alkoxy-$C_1$-$C_2$-alkyl, $C_1$-$C_2$-alkylthio-$C_1$-$C_2$-alkyl, benzyloxy-$C_1$-$C_3$-alkyl and benzylthio-$C_1$-$C_3$-alkyl.

Examples of the starting substances of the formula (VIII) which may be mentioned are: methanol, ethanol, propanol, isopropanol, butanol, isobutanol, sec-butanol, 2-methoxy-ethanol, 2-ethoxy-ethanol, 2-methylthio-ethanol, 2-ethylthio-ethanol, 2-benzyloxy-ethanol, 3-benzyloxy-propanol and 2-benzylthio-ethanol.

The starting substances of the formula (VIII) are known chemicals for synthesis.

Process (g) is preferably carried out using a diluent. Suitable diluents are mainly those which have already been mentioned in the description of process (a) according to the invention.

Process (g) is carried out in the presence of a mineral acid. Suitable mineral acids are preferably hydrochloric acid or sulphuric acid.

When carrying out process (g) according to the invention, the reaction temperatures may be varied within a relatively wide range. In general, the process is carried out at temperatures between 0° C. and 150° C., preferably at temperatures between 20° C. and 120° C.

The process according to the invention is generally carried out under atmospheric pressure.

For carrying out process (g), 1 to 10 moles, preferably 1.1 to 4 moles, of starting compound of the formula (VIII) and of the mineral acid are generally employed per mole of starting substance of the formula (I). In general, the reaction components are mixed together at room temperature or with slight cooling, and they are then stirred until the reaction is complete, if appropriate at an increased temperature. Working up can be carried out in a customary manner. For example, the reaction mixture is poured onto water and stirred or extracted with a virtually water-immiscible organic solvent, such as, for example, dichloromethane or toluene, and the organic phase is separated off, washed with water, dried and filtered. The filtrate is evaporated, and the product remaining in the residue can be purified in a customary manner.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon Weeds of the Genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon Cultures of the Genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon Weeds of the Genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon Cultures of the Genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are particularly suitable for the selective combating of dicotyledon weeds, especially in the post-emergence method.

The active compounds can be converted to tne customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, oorn cobs and tobacco stalks; as emulsifying and/or foam-forming agent there are suitable: for example non-ionic and anionic emulsifiers, such as poly-oxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione (amethydione) or N-(2-benzthiazolyl)-N,N'-dimethylurea (metabenzthiazuron) for combating weeds in cereals; 4-amino-3-methyl-6-phenyl-1,2,4-triazin-5(4H)-one (metamitron) for combating weeds in sugarbeets and 4-amino-6-(1,1-dimethylethyl)-3-methylthio-1,2,4-triazin-5(4H)-one (metribuzin) for combating weeds in soy beans, and furthermore 2,4-dichlorophenoxyacetic acid (2,4-D); 4-(2,4-dichlorophenoxy)-butyric acid (2,4-DB); 2,4-dichlorophenoxypropionic acid (2,4-DP); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl-5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-chloro-4-ethylamino-6-(3-cyanopropylamino-1,3,5-triazine (CYANAZINE); 3,6-dichloro-2-pyridinecarboxylic acid (CLOPYRALID); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl or its ethyl ester (FENOXAPROP); (trimethylsilylmethyl) 2-[4-(3,5-dichloropyrid-2-yloxy)-phenoxy]-propionate; methyl-2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzthiazol-2-yl-oxy)-acetanilide (MEFENACET ; 2-{[[((4-methoxy-6-methyl-1,3,5-triazin-2-yl)-amino)-carbonyl]amino]-sulphonyl}-benzoic acid or its methyl ester (METSULFURON); N-(1-ethylpropyl)-3,4-dimethyl-2,6-dinitroaniline (PENDIMETHALIN); 0-(6-chloro-3-phenylpyridazin-4-yl)-S-octyl-thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carbonate (THIAMETURON) and 3,5,6-trichloro-2pyridyloxyacetic acid (TRICLOPYR). Surprisingly, a few mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 15 kg per ha.

The preparation and use of the active compounds according to the invention can be seen from the following examples.

PREPARATION EXAMPLES

Example 1

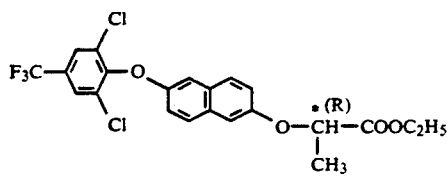

A mixture consisting of 16.8 g (0.045 mole) of 6-(2,6-dichloro-4-trifluoromethyl-phenoxy)-2-naphthol, 13.6 g (0.050 mole) of ethyl (S)-α-(4-methyl-phenylsulphonyloxy)-propionate, 6.3 g of potassium carbonate and 150 ml of acetonitrile is refluxed for 20 hours. The reaction mixture is cooled to approx. 20° C., diluted with water to approximately twice the volume, acidified with 1N hydrochloric acid and extracted with toluene. The organic phase is separated off, washed with water, dried over sodium sulphate and filtered. The solvent is carefully distilled off the filtrate in a water-pump vacuum.

5.9 g (28% of theory) of ethyl (R)-α-(6-(2,6-dichloro-4-trifluoromethyl-phenoxy)-naphthalen-2-yl-oxy)-propionate are obtained. Melting point: 118° C.-120° C.

In analogy with Example 1 and in accordance with the general description of the preparation processes according to the invention, the compounds of the formula (I) listed in Table 1 below can be prepared:

TABLE 1

Examples of the compounds of the formula (I)

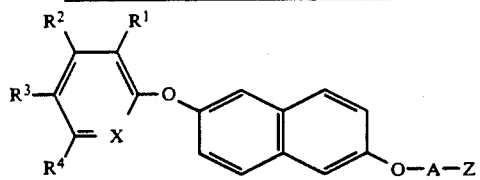

| Example No. | $R^1$ | $R^2$ | $R^3$ | $R^4$ | X | A | Z | Physical data |
|---|---|---|---|---|---|---|---|---|
| 2 | H | H | $CF_3$ | H | CH | $-CH(CH_3)-$ | $COOC_2H_5$ | $n_D^{20} = 1.5598$ |
| 3 | Cl | H | $CF_3$ | H | CH | $-CH(CH_3)-$ | $COOC_2H_5$ | m.p.: 84° C. |
| 4 | Cl | H | $CF_3$ | H | C—F | $-CH(CH_3)-$ | $COOC_2H_5$ | m.p.: 53° C. |
| 5 | Cl | Cl | $CF_3$ | H | C—Cl | $-CH(CH_3)-$ | $COOC_4H_9$ | |
| 6 | Cl | F | $CF_3$ | H | C—Cl | $-CH(CH_3)-$ | $COOCH(CH_3)_2$ | |
| 7 | Cl | H | $CF_3$ | H | C—Cl | $-CH_2-$ | $COOC_4H_9$ | |
| 8 | Cl | H | $CF_3$ | H | C—Cl | $-CH_2CH_2-$ | $COOCH_3$ | |
| 9 | Cl | H | $CF_3$ | H | C—Cl | $-CH(CH_3)-$ | COOH | |
| 10 | Cl | H | Cl | H | N | $-CH_2-$ | COOH | |
| 11 | Cl | H | Cl | H | N | $-CH(CH_3)-$ | COOH | |
| 12 | Cl | H | $CF_3$ | H | C—Cl | $-CH_2-$ | COOH | |
| 13 | Cl | H | Cl | H | N | $-CH(CH_3)-$ | $COOC_2H_5$ | |
| 14 | Cl | H | $CF_3$ | H | C—Cl | $-CH(CH_3)-$ | COCl | |
| 15 | Cl | H | $CF_3$ | H | C—Cl | $-CH(CH_3)-$ | $COO-CH_2-COOC_4H_9$ | |

TABLE 1-continued

Examples of the compounds of the formula (I)

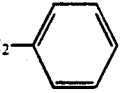 (I)

| Example No. | R¹ | R² | R³ | R⁴ | X | A | Z | Physical data |
|---|---|---|---|---|---|---|---|---|
| 16 | Cl | H | CF₃ | H | C—Cl | —CH(CH₃)— | COOCHCOOC₂H₅ \| CH₃ | |
| 17 | Cl | H | CF₃ | H | C—Cl | —CH₂— | COOCHCOOC₂H₅ \| CH₃ | |
| 18 | Cl | Cl | CF₃ | H | C—Cl | —CH₂— | COSC₂H₅ | |
| 19 | Cl | F | CF₃ | H | C—Cl | —CH(CH₃)— | COSCH₂COOCH₃ | |
| 20 | Cl | H | Cl | H | N | —CH₂C₂— | CONHC₂H₅ | |
| 21 | Cl | H | CF₃ | H | C—Cl | —CH₂— | COCl | |
| 22 | Cl | H | CF₃ | H | C—Cl | —CH₂CH₂— | COCl | |
| 23 | Cl | H | CF₃ | H | C—Cl | —CH₂CH₂— | COOH | |
| 24 | Cl | H | Cl | H | N | —CH₂CH₂— | COOH | |
| 25 | Cl | H | Cl | H | N | —CH(CH₃)— | COOCH₂CH₂OCH₃ | |
| 26 | Cl | H | CF₃ | H | C—Cl | —CH(CH₃)— | COOCH₂CH₂SC₂H₅ | |
| 27 | Cl | H | Cl | H | N | —CH₂— | COOCH₂—P(=O)(OC₂H₅)₂ | |
| 28 | Cl | H | CF₃ | H | C—Cl | —CH₂— | COOCH(C₆H₅)—P(=O)(OCH₃)₂ | |
| 29 | Cl | H | CF₃ | H | C—Cl | —CH₂CH₂— | CONHCH(CH₃)₂ | |
| 30 | Cl | Cl | CF₃ | H | C—Cl | —CH₂— | CON(C₂H₅)₂ | |
| 31 | Cl | F | CF₃ | H | C—Cl | —CH(CH₃)— | COOCH₂CH₂OCH₂—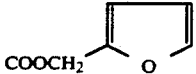 | |
| 32 | Cl | H | CF₃ | H | C—F | —CH(CH₃)— | COOCH₂-(furyl) | |
| 33 | Cl | H | Cl | H | N | —CH₂— | CONHOCH₃ | |
| 34 | Cl | H | CF₃ | H | C—Cl | —CH₂CH₂— | CO—NH—OC₂H₅ | |
| 35 | Cl | Cl | CF₃ | H | C—Cl | —CH(CH₃)— | CONHCH₂COOC₂H₅ | |
| 36 | CN | H | CF₃ | H | CH | —CH₂— | CONHNHSO₂CH₃ | |
| 37 | Cl | H | Cl | H | N | —CH₂— | COOCH₂Si(CH₃)₃ | |
| 38 | Cl | H | CF₃ | H | C—Cl | —CH(CH₃)— | COO(CH₂)₃OCH₂— | |

TABLE 1-continued

Examples of the compounds of the formula (I)

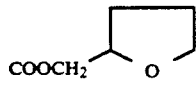

(I)

| Example No. | R¹ | R² | R³ | R⁴ | X | A | Z | Physical data |
|---|---|---|---|---|---|---|---|---|
| 39 | Cl | H | CF$_3$ | H | C—Cl | —CH$_2$— | CN | |
| 40 | Cl | H | CF$_3$ | H | C—Cl | —CH$_2$CH$_2$— | CN | |
| 41 | Cl | H | Cl | H | N | —CH$_2$— | CN | |
| 42 | Cl | Cl | CF$_3$ | H | C—Cl | —CH$_2$— | CN | |
| 43 | Cl | F | CF$_3$ | H | C—Cl | —CH$_2$— | CN | |
| 44 | Cl | H | CF$_3$ | H | C—F | —CH$_2$— | CN | |
| 45 | Cl | Cl | CF$_3$ | H | C—Cl | —CH(CH$_3$)— | COOC$_2$H$_5$ | |
| 46 | Cl | H | CF$_3$ | H | C—Cl | —CH(CH$_3$)— | COOCH$_3$ | |
| 47 | Cl | H | CF$_3$ | H | C—Cl | —CH$_2$CH$_2$— | COOC$_2$H$_5$ | |
| 48 | F | F | CF$_3$ | F | C—F | —CH(CH$_3$)— | COOC$_2$H$_5$ | |
| 49 | Cl | H | CF$_3$ | H | C—F | —CH(CH$_3$)— | COOH | |
| 50 | Cl | H | CF$_3$ | H | C—F | —CH(CH$_3$)— | COOCH$_2$Si(CH$_3$)$_3$ | |
| 51 | Cl | H | CF$_3$ | H | C—F | —CH(CH$_3$)— | COOCH$_2$P(O)(OC$_2$H$_5$)$_2$ | |
| 52 | Cl | H | CF$_3$ | H | C—Cl | —CH(CH$_3$)— | COOCH$_2$Si(CH$_3$)$_3$ | |
| 53 | Cl | H | CF$_3$ | H | C—Cl | —CH(CH$_3$)— | COOCH$_2$P(O)(OC$_2$H$_5$)$_2$ | |
| 54 | Cl | H | CF$_3$ | H | C—Cl | —CH(CH$_3$)— | COOCH$_2$CH$_2$OC$_2$H$_5$ | |
| 55 | Cl | H | CF$_3$ | H | C—Cl | —CH$_2$— | CO—NH$_2$ | |
| 56 | Cl | H | CF$_3$ | H | C—Cl | —CH$_2$— | CO—N(C$_3$H$_7$)$_2$ | |
| 57 | Cl | H | CF$_3$ | H | C—Cl | —CH$_2$— | CO—N(CH$_2$CH=CH$_2$)$_2$ | |
| 58 | Cl | H | CF$_3$ | H | C—Cl | (—CH$_2$)$_3$— | COOC$_2$H$_5$ | |
| 59 | Cl | H | CF$_3$ | H | C—Cl | —CH(C$_2$H$_5$)— | COOC$_2$H$_5$ | |
| 60 | Cl | H | CF$_3$ | H | C—Cl | —CH(CH$_3$)— | 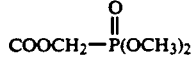 | |
| 61 | F | F | CF$_3$ | F | C—F | —CH(CH$_3$)— | COOCH$_2$—P(O)(OCH$_3$)$_2$ | |
| 62 | Cl | H | CF$_3$ | F | C—Cl | —CH(CH$_3$)— | COOCH(CH$_3$)—P(O)(OCH$_3$)$_2$ | |

TABLE 1-continued

Examples of the compounds of the formula (I)

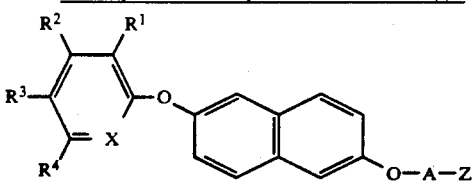

| Example No. | R¹ | R² | R³ | R⁴ | X | A | Z | Physical data |
|---|---|---|---|---|---|---|---|---|
| 63 | Cl | H | CF₃ | H | C—Cl | —CH(C₂H₅)— | COOC₂H₅ | |
| 64 | Cl | H | CF₃ | H | N | —CH(CH₃)— | COOH | |
| 65 | H | H | CF₃ | H | N | —CH₂— | COOH | |
| 66 | Cl | H | CF₃ | H | CH | —CH(CH₃)— | COOCH₃ | |

Starting substances of the formula (II)

Example (II-1)

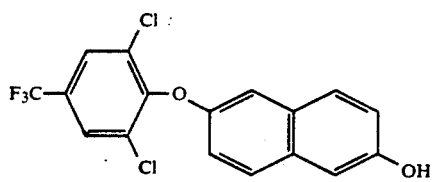

46.8 g (0.19 mole) of 3,4,5-trichloro-benzotrifluoride are added slowly and with stirring to a mixture which consists of 56.8 g (0.36 mole) of 2,6-dihydroxynaphthalene, 14.3 g (0.36 mole) of pulverulent sodium hydroxide and 170 ml of dimethyl sulphoxide and which has been heated to 120° C., and the reaction mixture is then stirred at 120° C. for approximately 3 hours and further at 20° C. for approximately 15 hours. The reaction mixture is then diluted with water to twice the volume, and acidified with 1N hydrochloric acid. The precipitate obtained is separated off and extracted with toluene, and the organic phase is separated off, washed with water, dried over sodium sulphate and filtered. The solvent is distilled off the filtrate in a waterpump vacuum. The residue is recrystallized from ethanol.

52 g (74% of theory) of 6-(2,6-dichloro-4-trifluoromethyl-phenoxy)-2-naphthol of melting point 158° C. are obtained.

The starting substances of the formula (II) listed in Table 2 below can be prepared in analogy with Example (II-1).

(II)

R² R¹
R³———O———naphthyl———OH
R⁴ X

TABLE 2

Examples of the starting substances of the formula (II)

| Example No | R¹ | R² | R³ | R⁴ | X | Physical data |
|---|---|---|---|---|---|---|
| II-2 | Cl | H | CF₃ | H | C—H | m.p.: 107° C. |
| II-3 | H | H | CF₃ | H | C—H | |
| II-4 | Cl | Cl | CF₃ | H | C—Cl | |
| II-5 | Cl | F | CF₃ | H | C—Cl | |
| II-6 | Cl | H | CF₃ | H | C—F | |
| II-7 | CN | H | CF₃ | H | CH | |
| II-8 | Cl | H | Cl | H | N | |
| II-9 | Cl | H | CF₃ | H | N | |
| II-10 | H | H | CF₃ | H | N | |

Use Examples

In the following use examples, the compound listed below is used as a comparison substance:

(A)

Cl—C₆H₃(Cl)—O—C₆H₄—O—CH(CH₃)—COOCH₃ methyl α-(4-(2,4-dichloro-phenoxy)-phenoxy)-propionate (disclosed in DE-OS (German Published Specification) 2,223,894/Example 86).

Example

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the compounds of Preparation Examples (1), (2) and (3), for example, show a considerably better action against problem weeds, such as, for example, Abutilon, Chenopodium, Galinsoga, Portulak and Viola than the comparison substance (A), while at the same time showing high selectivity in corn and wheat.

It is understood that the specification and examples are illustrative but not limitative of the present invention and that other embodiments within the spirit and scope of the invention will suggest themselves to those skilled in the art.

We claim:

1. A (6-aryloxy-naphthalen-2-yl-oxy)-alkane-carboxylic acid derivative of the formula

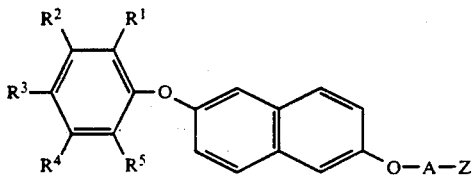

in which
R$^1$ stands for hydrogen, halogen or trifluoromethyl,
R$^2$ stands for hydrogen or halogen,
R$^3$ stand for halogen or trifluoromethyl
R$^4$ stands for hydrogen or halogen,
R$^5$ stands for halogen,
A stands for optionally branched alkanediyl and
Z stands for —CO—Y,
wherein
Y stands for halogen, hydroxyl.

2. A (6-aryloxy-naphthalen-2-yl-oxy)-alkanecarboxylic acid derivative according to claim 1, in which
R$^1$ stands for hydrogen, fluorine, chlorine, bromine or trifluoromethyl,
R$^2$ stands for hydrogen, fluorine or chlorine
R$^3$ stands for fluorine, chlorine, bromine or trifluoromethyl,
R$^4$ stands for hydrogen, fluorine or chlorine,
R$^5$ stands for fluorine, chlorine or bromine,
A stands for optionally branched C$_1$-C$_4$-alkanediyl and
Z stands for the grouping —CO—Y, wherein
Y stands for chlorine, hydroxyl.

3. A (6-hetero)aryloxy-naphthalen-2-yl-oxy)-alkanecarboxylic acid derivative according to claim 1, in which
R$^1$ stands for fluorine or chlorine,
R$^2$ stands for hydrogen, fluorine or chlorine,
R$^3$ stands for chlorine or trifluoromethyl,
R$^4$ stands for hydrogen, fluorine or chlorine,
R$^5$ stands for fluorine or chlorine,
A stands for methylene (—CH$_2$—), dimethylene (—CH$_2$CH$_2$—), trimethylene (—CH$_2$—)$_3$ or ethylidene

and
Z stands for the grouping —CO—Y, wherein
Y stands for chlorine or hydroxyl.

4. The compound ethyl (R) α-(6-(2,6-dichloro-4-trifluoromethyl-phenoxy)-naphthalen-2-yl-oxy)-propionate of the formula

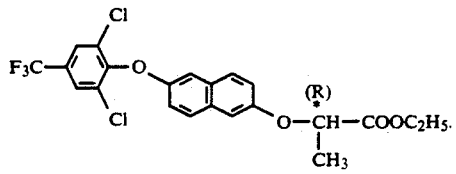

5. The compound ethyl α-(6-(2-chloro-4-trifluoromethyl-phenoxy)-naphthalen-2-yl-oxy)-propionate of the formula

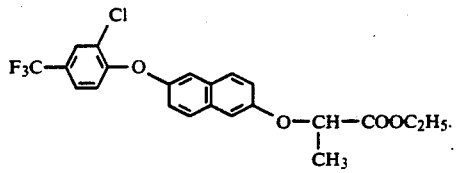

6. A herbicidal composition comprising a herbicidally effective amount of a compound according to claim 1 and a diluent.

7. A method of combating unwanted vegetation which comprises applying to such vegetation or to a locus from which it is desired to exclude such vegetation a herbicidal composition comprising a herbicidally effective amount of a compound according to claim 1.

8. The method according to claim 7, wherein such compound is
ethyl (R) α-(6-(2,6-dichloro-4-trifluoromethyl-phenoxy)-naphthalen-2-yl-oxy)-propionate, or
ethyl α-(2-chloro-4-trifluoro-methyl-phenoxy)-naphthalen-2-yl-oxy)-pripionate.

* * * * *

UNITED STATES PATENT AND TRADEMARK OFFICE
CERTIFICATE OF CORRECTION

PATENT NO.  : 5,079,384

DATED       : January 7, 1992

INVENTOR(S) : Haug et al.

It is certified that error appears in the above-identified patent and that said Letters Patent is hereby corrected as shown below:

Title Page      ABSTRACT: Line 8 delete " trifluomethoxy " and substitute -- trifluoromethoxy --

Col. 29, line 47      After " hydroxyl " delete " . " and substitute -- , or for the grouping $-O-R^6$, wherein $R^6$ stands for an optionally halogen-substituted radical from the group consisting of alkyl, alkenyl, alkinyl. --

Signed and Sealed this

Thirteenth Day of July, 1993

Attest:

MICHAEL K. KIRK

Attesting Officer      Acting Commissioner of Patents and Trademarks